United States Patent
Allen, Jr. et al.

(10) Patent No.: US 7,375,063 B2
(45) Date of Patent: May 20, 2008

(54) STRUCTURED BODY WASH

(75) Inventors: Aberdeen Allen, Jr., Parlin, NJ (US); Subhash Harmalker, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 166 days.

(21) Appl. No.: 11/186,509

(22) Filed: Jul. 21, 2005

(65) Prior Publication Data
US 2006/0019862 A1    Jan. 26, 2006

Related U.S. Application Data

(60) Provisional application No. 60/589,839, filed on Jul. 21, 2004.

(51) Int. Cl.
- C11D 1/94 (2006.01)
- C11D 3/37 (2006.01)
- C11D 9/18 (2006.01)
- A61K 8/00 (2006.01)

(52) U.S. Cl. ............. 510/130; 510/155; 510/159; 510/426; 510/433; 510/476; 510/490; 510/492; 510/499; 424/401; 424/70.16; 424/70.19; 424/70.21; 424/70.22

(58) Field of Classification Search ........... 510/130, 510/155, 159, 426, 433, 476, 490, 492, 499; 424/401, 70.16, 70.19, 70.21, 70.22
See application file for complete search history.

(56) References Cited

U.S. PATENT DOCUMENTS

| | | | |
|---|---|---|---|
| 4,457,856 A | * | 7/1984 | Mitchell et al. ............ 510/236 |
| 5,534,265 A | | 7/1996 | Fowler et al. |
| 5,658,577 A | | 8/1997 | Fowler et al. |
| 5,681,801 A | | 10/1997 | Zocchi |
| 5,830,445 A | | 11/1998 | Bouillon et al. |
| 5,866,529 A | | 2/1999 | Erilli et al. |
| 5,888,521 A | | 3/1999 | Zimmerman |
| 5,888,951 A | | 3/1999 | Gagnebien et al. |
| 5,928,657 A | | 7/1999 | Simon |
| 5,932,234 A | | 8/1999 | Simon et al. |
| 6,033,680 A | | 3/2000 | Dixon et al. |
| 6,051,541 A | | 4/2000 | Neuser et al. |
| 6,165,510 A | | 12/2000 | Baines et al. |
| 6,277,797 B1 | | 8/2001 | Glenn, Jr. et al. |
| 6,294,179 B1 | | 9/2001 | Lee et al. |
| 6,294,509 B1 | | 9/2001 | Meiwa et al. |

(Continued)

FOREIGN PATENT DOCUMENTS

CA    2 306 376    10/2000

(Continued)

OTHER PUBLICATIONS

Svelto Gel Microgranuli Strawberry Product Information retrieved from www.Unilever.com 2005 (No Month Given).

(Continued)

Primary Examiner—Brian P Mruk
(74) Attorney, Agent, or Firm—Michael F Morgan

(57) ABSTRACT

Novel cleansing compositions and methods for making same are described. Preferred embodiments provide compositions comprising an aqueous acrylate copolymer emulsion; an anionic surfactant; and an amphoteric surfactant. Amphoteric surfactants useful herein include betaine surfactants.

15 Claims, 1 Drawing Sheet

U.S. PATENT DOCUMENTS

| | | |
|---|---|---|
| 6,339,058 B1 | 1/2002 | Toussaint et al. |
| 6,362,156 B1 | 3/2002 | Hsu et al. |
| 6,369,018 B1 | 4/2002 | Hsu et al. |
| 6,380,150 B1 | 4/2002 | Toussaint et al. |
| 6,391,863 B1 | 5/2002 | Philippe et al. |
| 6,395,691 B1 | 5/2002 | Tsaur |
| 6,461,599 B1 | 10/2002 | Ruben |
| 6,635,702 B1 * | 10/2003 | Schmucker-Castner et al. ............ 524/291 |
| 6,638,519 B1 | 10/2003 | Lorant |
| 6,767,878 B1 | 7/2004 | Paye et al. |
| 6,846,785 B2 | 1/2005 | Patel et al. |
| 6,927,201 B2 | 8/2005 | Hsu et al. |
| 6,972,278 B2 | 12/2005 | Hsu et al. |
| 7,022,657 B2 | 4/2006 | Hines et al. |
| D529,398 S | 10/2006 | Van Dingenen |
| 2002/0123438 A1 | 9/2002 | Pflederer et al. |
| 2003/0044442 A1 | 3/2003 | Stanier et al. |
| 2003/0171230 A1 | 9/2003 | Shana'a et al. |
| 2004/0018950 A1 | 2/2004 | Foley et al. |
| 2004/0186037 A1 | 9/2004 | Cheung et al. |
| 2005/0020467 A1 | 1/2005 | Kinscherf |
| 2005/0020471 A1 | 1/2005 | Cheung et al. |
| 2005/0043200 A1 | 2/2005 | Barry et al. |
| 2005/0100570 A1 | 5/2005 | Wei et al. |
| 2005/0106112 A1 | 5/2005 | Boyd et al. |
| 2005/0170982 A1 | 8/2005 | Boone et al. |
| 2005/0176613 A1 | 8/2005 | Wai et al. |
| 2005/0203213 A1 | 9/2005 | Pommiers et al. |
| 2005/0245419 A1 | 11/2005 | Guzmann et al. |
| 2006/0019861 A1 * | 1/2006 | Potechin et al. ............ 510/475 |
| 2006/0083761 A1 | 4/2006 | Yoshimi et al. |
| 2006/0194709 A1 | 8/2006 | Boone et al. |
| 2007/0009463 A1 | 1/2007 | Niebauer et al. |
| 2007/0010415 A1 | 1/2007 | Kinscherf et al. |
| 2007/0066507 A1 | 3/2007 | Fleckenstein et al. |

FOREIGN PATENT DOCUMENTS

| | | |
|---|---|---|
| EP | 0 452 106 | 10/1991 |
| EP | 1 090 631 | 4/2001 |
| WO | WO 94/05757 | 3/1994 |
| WO | WO 97/26315 | 7/1997 |
| WO | WO 99/60996 | 12/1999 |
| WO | WO 02/38720 | 5/2002 |
| WO | WO 03/099986 | 12/2003 |
| WO | WO 2006/021255 | 5/2006 |

OTHER PUBLICATIONS

Analysis of Cif Gel product sold in Europe No Date Given.
Analysis of Svelto Gel product sold in Europe No Date Given.
U.S. Appl. No. 60/870,296, filed Dec. 15, 2006, Tuzi et al.
U.S. Appl. No. 60/870,496, filed Dec. 18, 2006, Tuzi et al.

* cited by examiner

STRUCTURED BODY WASH

CROSS-REFERENCE TO RELATED APPLICATIONS

This application claims benefit of U.S. Provisional Application No. 60/589,839, filed Jul. 21, 2004, the disclosure of which is hereby incorporated by reference herein in its entirety.

FIELD OF THE INVENTION

This invention relates, to improved cleansing compositions.

BACKGROUND OF THE INVENTION

U.S. Pat. No. 6,635,702 B1 describes Stable Aqueous Surfactant Compositions.

U.S. patent application 2002/0123438 A1 describes Clear Cleansing Detergent Systems.

BRIEF SUMMARY OF THE INVENTION

The present invention is directed, in part, to novel cleansing compositions and methods for making same. Specifically, in certain embodiments, there are provided cleansing compositions comprising an aqueous acrylate copolymer emulsion; an anionic surfactant; and an amphoteric surfactant.

DETAILED DESCRIPTION OF THE INVENTION

Figure 1:
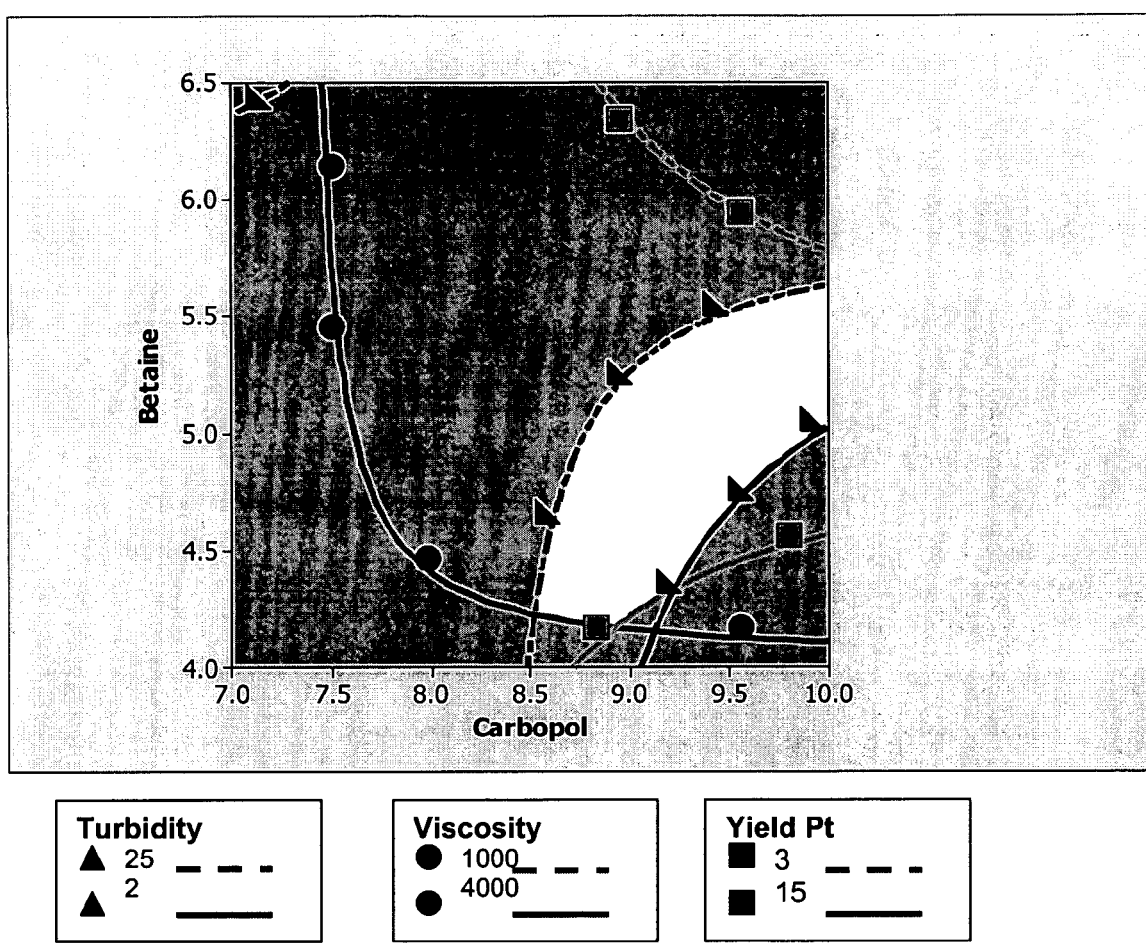
FIG. 1 shows a plot of the concentration of a selected acrylate copolymer and of cocamidopropyl betaine for selected properties.

In certain embodiments, this invention comprises a cleansing composition comprising:

(a) an aqueous acrylate copolymer emulsion, preferably about 2.6% to about 3% by weight of the total composition (% in active amounts of the composition);

(b) an anionic surfactant, preferably about 7.7% to about 10.2% by weight of the total composition; and (c) an amphoteric surfactant, preferably about 1.4% to about 1.7% by weight of the total composition.

Optionally, a pearlizing agent, preferably about 0.5% by weight of the total composition, may be present in the composition. A non-limiting example of such an agent is ethylene glycol distearate.

Optionally, effective amounts of one or more ingredients selected from the group consisting of colorants, fragrances, antibacterials, preservatives, antioxidants, beads (fragrance, exfoliating or moisturizing), mica, glitter, opacifying agents, pearlizing agents, and mixtures thereof may be present in the composition.

In certain embodiments, the composition has a high clarity, preferably in the range of about 2 to about 25 NTU's. In certain embodiments, the composition has a viscosity preferably in the range of about 4,000 to about 10,000 centipoise. In certain embodiments, the composition has a yield value preferably in the range of about 3 to about 15 Pascals whereby a post added ingredient is suspended with a uniformity of distribution and a stability of a minimum of about 8 months at 49 degrees C.

In certain embodiments, this invention comprises a non-emulsified structured liquid personal cleansing composition providing enhanced performance. In certain embodiments, the composition comprises:

(a) about 8.5 to about 10.00 weight % of 30% active (for example, in water) or its equivalent in active amounts (preferably 8.95 weight percent from the listed range) of an aqueous acrylate copolymer emulsion (as a non-limiting example, see U.S. Pat. No. 6,635,702, such as a composition wherein the copolymer is derived from:

a-1. about 35% to about 65% by weight of acrylic acid or methacrylic acid, or combinations thereof, b-1. about 65% to about 35% by weight of ethylacrylate, or methylacrylate, or combinations thereof, and c-1. about 0.03% to about 3% by weight of polyalkenyl ethers of sucrose or polyalcohols; or trimethylolpropane tri(meth)acrylate, glycidyl methacrylate, N-methylolacrylamide, or combinations thereof);

(b) about 30 to about 40 weight % of 25.5% active (for example, in water) of an anionic surfactant (or its equivalent in active amounts). Non-limiting examples include sodium laureth sulfate and sodium pareth sulfate, preferably in an amount of 37.13% from the listed range);

(c) about 4.5 to about 5.7 weight % of 30% active (for example, in water) of an amphoteric surfactant or a betaine or its equivalent in active amounts (including without limitation cocoamidopropyl betaine such as in an amount of about 5.64% of the 30% active material);

(d) optionally a pearlizing agent such as, for example, about 2 weight % of 25% active or its equivalent in active amounts (for example, in water and surfactant) of ethylene glycol distearate;

(e) optionally, effective amounts of optional ingredients such as colorants, fragrances, antibacterials, preservatives, antioxidants, beads (fragrance, exfoliating or moisturizing), mica, glitter, opacifying agents, pearlizing agents and other such ingredients. Preferably, the composition has high clarity (about 2 to about 25 NTU's), a targeted viscosity (about 4,000 to about 10,000 centipoise) for ease of dispensing from an orifice in the range of about ¼ to about ⅛, and a yield value (about 3 to about 15 Pascals) that allows the composition to suspend a variety of post added ingredients with a uniformity of distribution and enhanced stability (for example, about 8 months at 120 degrees F. (49 degrees C.)).

One particular embodiment comprises shea butter beads in the range of about 100 to about 1200 microns in diameter. Another particular embodiment comprises polyethylene beads in the size range of about 200 to about 1000 microns as an exfoliant (for example in an amount of about 0.01 to about 2 weight %), or larger polyethylene beads (about 250 to about 2000 microns) in smaller amounts (for example, in an amount of about 0.01 to about 1 weight %).

The polymetric rheology modifier provides several properties such as flow, thickening, viscosity, suspending ability and yield value. For our purpose yield value also referred to as yield point is defined as the initial resistance to flow under stress. It can be measured using a constant stress rheometer Brookfield YR-1 Yield Rheometer using a #72 spindle at an appropriate rotational speed. A preferred range of the yield point is about 3 to about 15 Pa.

The turbidity (clarity) of the present cleaning composition is determined by using a Hach 2100P Turbidimeter. A preferred range is about 2 to about 25 NTU's The viscosity of the present cleansing composition is preferably in the range of about 4,000 to about 10,000 cps as determined using a Brookfield DV-II+ Viscometer using a #5 spindle at an appropriate rotational speed (between 10-30 RPM).

In certain embodiments, one of the major advantages of the compositions of the invention is the significant improvement in clarity that is achieved.

Note that the amounts of active ingredient may be varied on the basis of a recited solution, but the same amounts of actives may be added via different dilutions.

Examples of suitable anionic surfactants include, but are not limited to, alkyl sulfates, ethoxylated alkyl sulfates, alkyl sulfonates, alkyl olefin sulfonates, alkyl succinates, alkyl sulfosuccinates, alkyl ethoxy sulfosuccinates, acyl and alkyl glutamates, alkyl phosphates, alkyl ether carboxylates, alkyl isethionates, acyl amides.

Suitable amphoteric surfactants include, but are not limited to, betaine surfactants. Examples of suitable amphoteric surfactants include, but are not limited to, alkyl betaines, alkylamido betaines, alkyl sulfobetaines, alkyl sultaines and alkylamido sultaines; preferably, those having about 8 to about 18 carbons in the alkyl and acyl group.

Suitable acrylate copolymers include, but are not limited to, those described in U.S. Pat. No. 6,635,702 B1 (hereby incorporated herein by reference) as described above and, in more general terms, those selected from the group consisting of:

(a) monomers or copolymers of one or more of methacrylic acid, acrylic acid, itaconic acid, esters of any of the foregoing and mixtures of any of the foregoing;

(b) a member of group (a) copolymerized with one or more members selected from the group consisting of Steareth-20, Steareth-50, Ceteth-20.

Examples of suitable acrylate copolymers include those sold under the tradenames CARBOPOL® AQUA SF-1 from Noveon (Cleveland, Ohio), SYNTHALEN® W2000 from 3V (Wehawkin, N.J.), ACULYN® 22, and ACULYN®33 available from International Specialty Products Corporation (Wayne, N.J.).

Alkaline neutralizing agents include, with out limitation, inorganic and organic neutralizers selected from the group consisting of alkali hydroxides and alkanolamines, sodium hydroxide and triethanolamine.

While the compositions of the invention may be made with or without a suspending agent such as, without limitation, glycol stearates, glycol distearates such as ethylene glycol distearate, one embodiment is free of any additional suspending agents.

Compositions according to the invention can be made using conventional mixing techniques known to those skilled in the art for mixing ingredients, such as described, for example, in Example 1.

General Making Procedure:

1. Disperse Acrylates copolymer into room temperature water with propeller agitation.
2. Add an anionic surfactant or its equivalent (for example, sodium laureth sulfate, sodium pareth sulfate) and mix until uniform.
3. Neutralize with sodium hydroxide to pH 6.6-6.8
4. Add amphoteric surfactants (for example cocoamidopropyl betaine)
5. Add any pearlizing ingredients
6. Add colors, fragrance and preservatives.
7. If needed add sodium chloride to increase viscosity
8. Add citric acid if needed to adjust pH.

The invention will be better understood by reference to the following examples which serve to demonstrate but not limit the scope of the present invention.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application values for n, m, etc. in formulas, molecular weights and degree of ethoxylation or propoxylation are averages. Temperatures are in degrees C. unless otherwise indicated. The amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., 7th ed. 1997).

General Method

In some of the following examples the formulations are prepared as follows. The acrylates copolymer are added to water and mixed. Then the anionic surfactant or its equivalent is added to the aqueous polymer composition and mixed. Next a neutralizing agent is added and mixed. Subsequently, the amphoteric surfactant(s) are added and mixed. The remaining ingredients are then added in the order listed with mixing upon the addition of each ingredient. Optionally, an acid such as citric acid is added and mixed.

Example 1

The general method described above may be used to make a product of the invention with the types and amounts of the following ingredients:

| Ingredient | Weight % |
| --- | --- |
| Deionized water | qs. |
| Sodium Laureth Sulfate | 37.13 |
| Acrylates Copolymer | 8.95 |
| Sodium hydroxide | 0.74 |
| Cocoamidopropylbetaine | 5.64 |
| DMDM Hydantion | 0.4 |
| EDTA | 0.211 |

Example 2

The general method described above may be used to make a product of the invention with the types and amounts of the following ingredients:

| Ingredient | Weight % |
| --- | --- |
| Deionized water | qs. |
| Sodium Laureth Sulfate | 37.13 |
| Acrylates Copolymer | 8.95 |
| Sodium hydroxide | 0.74 |
| Cocoamidopropylbetaine | 5.64 |

-continued

| Ingredient | Weight % |
| --- | --- |
| DMDM Hydantion | 0.4 |
| EDTA | 0.211 |

Example 3

FIG. 1 shows a plot of the concentration of a selected acrylate copolymer and cocamidopropyl betaine for selected properties whereby the white unshaded area bounds the formulations of high clarity (2-25 NTU's), targeted viscosity (4,000-10,000 cps) for ease of dispensing from an orifice in the range of ¼-⅛, and a yield value (3-15) that allows the composition to suspend a variety of post added ingredients with a uniformity of distribution and enhanced stability (for example, 8 months at 120 degrees F. (49 degrees C.)). It has been noted that there is a small pocket of good viscosity and clarity at a betaine level of 6.5-7.0, but the yield point is not satisfactory.

Additional Examples

The general method described above for Examples 1 and 2 may be repeated with the use of additional ingredients such as one or more of:
1.5-2.5 (particularly 2) weight % ethylene glycol distearate (at 30% active) or an equivalent amount
0.01-2 (particularly 1) weight % of polyethylene beads (size in the range of 200 -1000 microns)
0.01-1 (particularly 0.5) weight % of a larger size polyethylene beads (in the range of 250-2000 microns).

All numerical ranges described herein include all combinations and subcombinations of ranges and specific integers encompassed therein.

Various modifications of the invention, in addition to those described herein, will be apparent to those skilled in the art from the foregoing description. Such modifications are also intended to fall within the scope of the appended claims.

What is claimed:
1. A cleansing composition comprising:
    a) about 2.6% to about 3% by weight of an aqueous acrylate copolymer emulsion;
    b) about 7.7% to about 10.2% by weight of an anionic surfactant;
    c) about 1.4% to about 1.7% by weight of an amphoteric surfactant; and
    d) an effective amount of shea butter beads, each bead having a diameter of about 100 to about 1200 microns.
2. The composition of claim 1 wherein the composition has a clarity in the range of about 2 to about 25 NTUs.
3. The composition of claim 1 wherein the composition has a viscosity in the range of about 4,000 to about 10,000 centipoise.
4. The composition of claim 1 wherein the composition has a yield value in the range of about 3 to about 15 Pascals; wherein a post added ingredient is suspended with a uniformity of distribution and a stability of a minimum of about 8 months at 49 degrees C.
5. The composition of claim 1 further comprising a pearlizing agent.
6. The composition of claim 5, wherein the pearlizing agent is ethylene glycol distearate.
7. The composition of claim 1 wherein the amphoteric surfactant is a betaine surfactant.
8. The composition of claim 1 further comprising effective amounts of one or more ingredients selected from the group consisting of colorants, fragrances, antibacterials, preservatives, antioxidants, polyethylene beads, mica, glitter, opacifying agents, pearlizing agents!and combinations thereof.
9. The composition of claim 8, wherein the polyethylene beads have a diameter of about 250 to about 2000 microns.
10. The composition of claim 8, wherein the polyethylene beads have a diameter of about 200 to about 1000 microns.
11. The composition of claim 1 wherein the copolymer comprises:
    a) about 35% to about 65% by weight of acrylic acid or methacrylic acid, or combinations thereof;
    b) about 65% to about 35% by weight of ethylacrylate, or methylacrylate, or combinations thereof; and
    c) about 0.03% to about 3% by weight of polyalkenyl ethers of sucrose or polyalcohols; or trimethylolpropane tri(meth)acrylate, glycidyl methacrylate, N-methylolacrylamide, or combinations thereof.
12. A cleansing composition comprising:
    a) about 2.6% to about 3% by weight of an aqueous acrylate copolymer emulsion;
    b) about 7.7% to about 10.2% by weight of an anionic surfactant;
    c) about 1.4% to about 1.7% by weight of an amphoteric surfactant; and
    d) an effective amount of shea butter beads, each bead having a diameter of about 100 to about 1200 microns
wherein the composition has a high clarity in the range of about 2 to about 25 NTUs, a viscosity in the range of about 4,000 to about 10,000 centipoise, and a yield value in the range of about 3 to about 15 Pascals; wherein a post added ingredient is suspended with a uniformity of distribution and a stability of a minimum of about 8 months at 490C.
13. A method of making the cleansing composition of claim 12 comprising the steps of:
    a) dispersing acrylates copolymer into room temperature water with propeller agitation;
    b) adding an anionic surfactant to the result of step a);
    c) mixing the result of step b) until a uniform mixture is formed;
    d) neutralizing the mixture of step c) with sodium hydroxide to a pH of about 6.6 to about 6.8;
    e) adding an amphoteric surfactant to the result of step d); and
    f) mixing in the shea butter beads.
14. The composition of claim 1, wherein the beads are present in an amount of about 0.01% to about 1% by weight.
15. The composition of claim 1, wherein the beads are present in an amount of about 0.01% to about 2% by weight.

* * * * *